United States Patent [19]
Caizza et al.

[11] Patent Number: 6,036,674
[45] Date of Patent: Mar. 14, 2000

[54] RETRACTING NEEDLE SYRINGE

[75] Inventors: Richard J. Caizza, Barry Lakes; Robert Cipoletti, Paterson, both of N.J.

[73] Assignee: Becton Dickinson and Company, Franklin Lakes, N.J.

[21] Appl. No.: 09/216,412

[22] Filed: Dec. 18, 1998

[51] Int. Cl.[7] ................................................ A61M 5/00
[52] U.S. Cl. ............................................ 604/195; 604/110
[58] Field of Search .................................. 604/110, 187, 604/192, 195, 198, 263

[56] References Cited

U.S. PATENT DOCUMENTS

| | | | |
|---|---|---|---|
| 4,687,467 | 8/1987 | Cygielski | 604/110 |
| 4,838,869 | 6/1989 | Allard | 604/195 |
| 5,019,044 | 5/1991 | Tsao | 604/110 |
| 5,049,133 | 9/1991 | Villen Pascual | 604/110 |
| 5,053,010 | 10/1991 | McGary et al. | 604/110 |
| 5,180,369 | 1/1993 | Dysarz | 604/110 |
| 5,180,370 | 1/1993 | Gillespie | 604/110 |
| 5,188,597 | 2/1993 | Sweeney et al. | 604/110 |
| 5,201,710 | 4/1993 | Caselli | 604/110 |
| 5,273,543 | 12/1993 | Bell et al. | 604/110 |
| 5,395,337 | 3/1995 | Clemens et al. | 604/110 |
| 5,407,436 | 4/1995 | Toft et al. | 604/195 |
| 5,533,970 | 7/1996 | Berger et al. | 604/110 |
| 5,769,822 | 6/1998 | McGary et al. | 604/110 |

FOREIGN PATENT DOCUMENTS 2 197 792  11/1986  United Kingdom .

*Primary Examiner*—John D. Yasko
*Attorney, Agent, or Firm*—John L. Voellmicke

[57] ABSTRACT

A retracting needle syringe includes a barrel having a chamber, an open proximal end and an open distal end. A plunger is slidably positioned in fluid-tight engagement with an inside surface of the barrel. The plunger has an elongated cavity in its distal end and a cover element sealing the cavity. A needle assembly at the distal end of the barrel includes a needle cannula having an inner hub having an open proximal end and a distal end connected to the needle cannula so that the lumen of the cannula is in fluid communication with the chamber. A flange on the inner hub is connected to a proximal end of an outer hub so that the needle cannula projects distally outwardly from a distal end of the outer hub. A spring is contained between the inner hub and the outer hub. A circular release element is movably connected to a proximal end of the flange. The release element has a distal end and a sharp proximal end projecting into the chamber, wherein distal motion of the plunger will cause the sharp proximal end to cut through the cover element and the distal end of the release element to dissociate an outer portion of the flange from an inner portion of the flange allowing the spring to expand and move the needle cannula into the cavity.

34 Claims, 9 Drawing Sheets

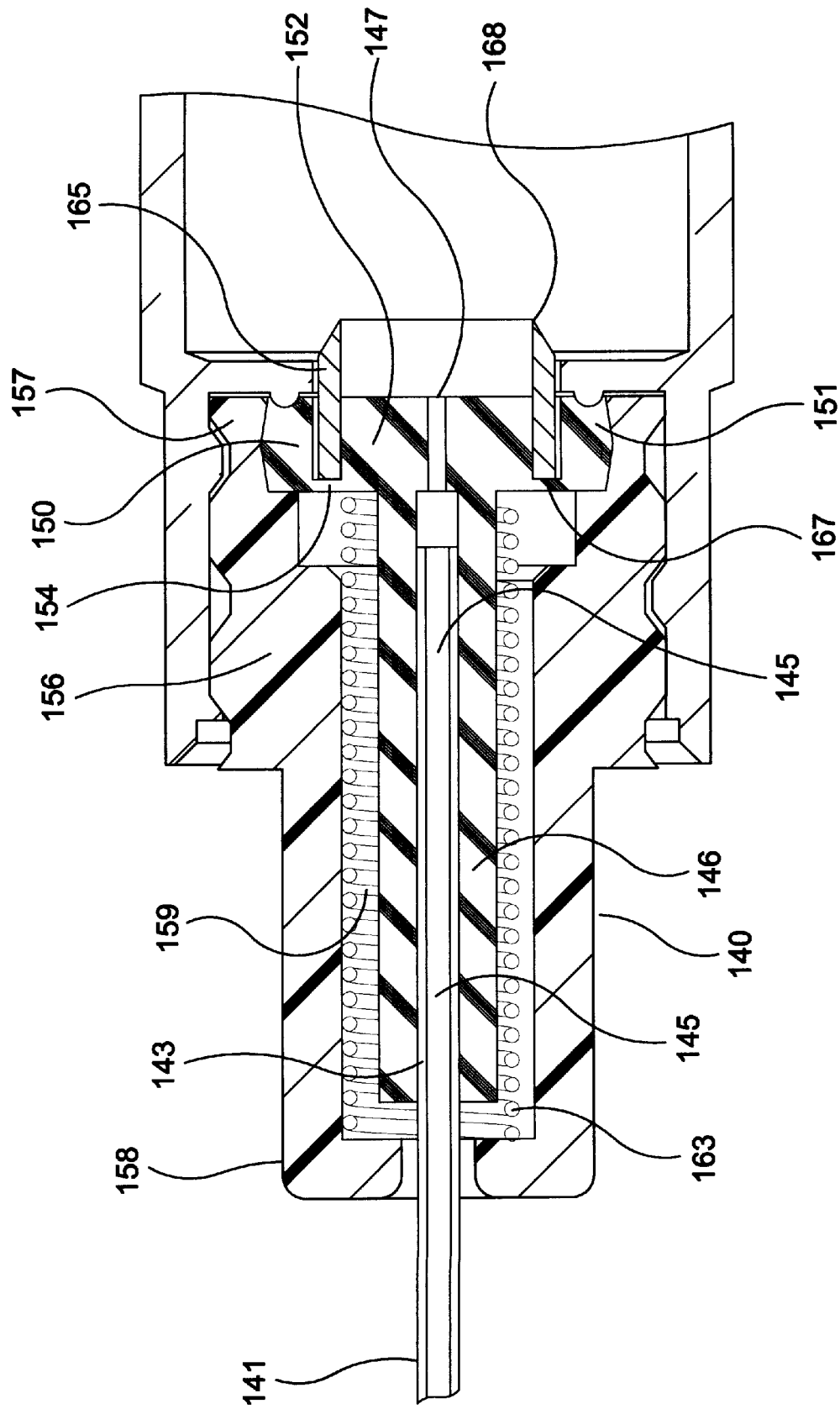

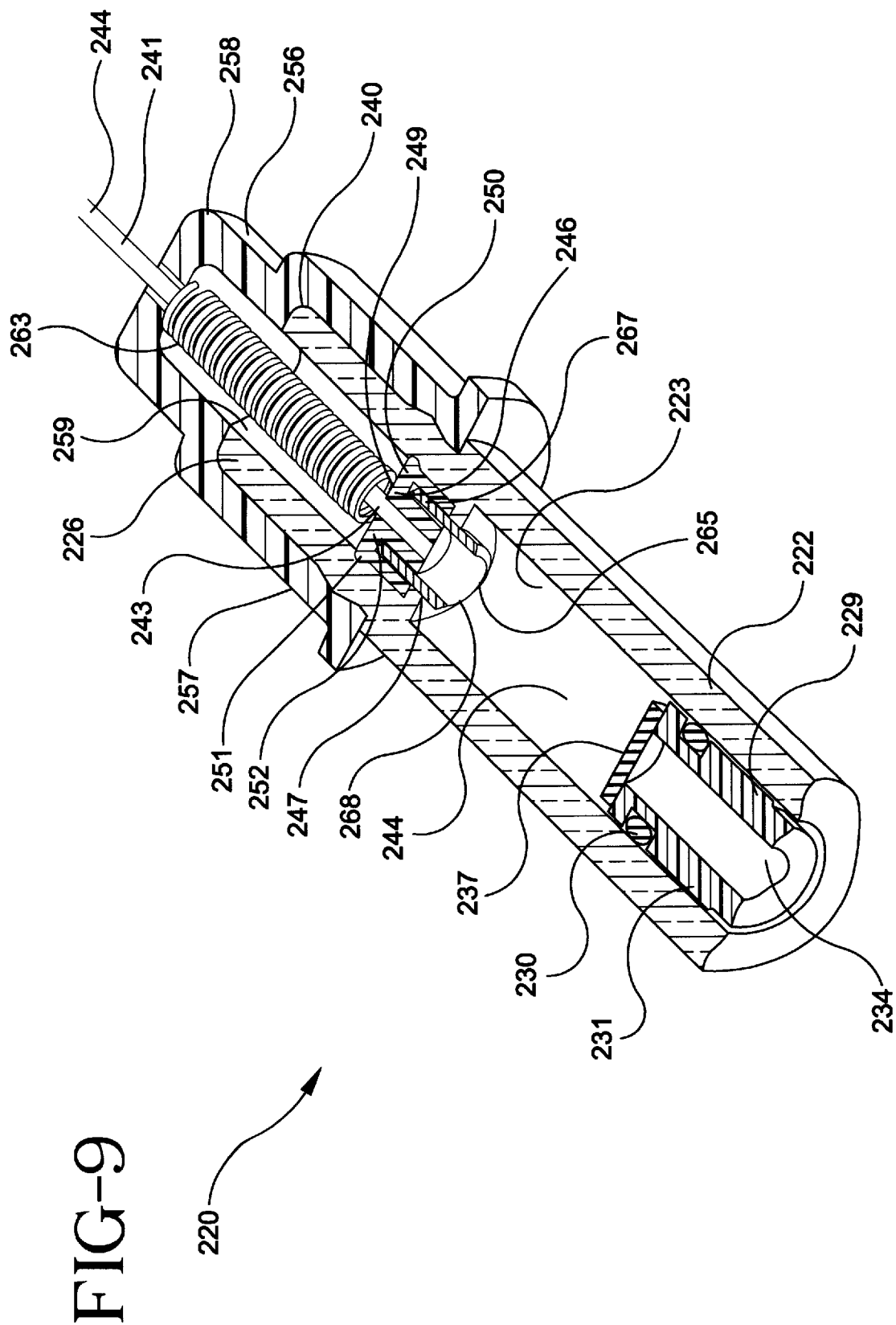

RETRACTING NEEDLE SYRINGE

FIELD OF THE INVENTION

The present invention relates to syringes and needle assemblies. More particularly, the present invention relates to a syringe and needle assembly having structure allowing for the automatic withdrawal of the needle cannula into the syringe barrel after use.

BACKGROUND

In recent years there has developed an increased concern regarding the transfer of disease, infection or the like to syringe users and healthcare professionals who accidentally or through negligent handling stick themselves with hypodermic needles while disposing of used hypodermic needle containing products. In many areas in a hospital, where needle cannula products are used, disposal bins are provided so that a syringe or other needle cannula product may be immediately discarded in a safe rigid container. However, there are areas of medical practice, such as emergency rooms, where disposal containers may not be readily available or practical, and where products having self-contained safety features are desirable. In theory, after such a syringe is used to inject medication or for another purpose, a safety device contained within the syringe or needle assembly is activated to prevent further contact with the sharp needle tip. One type of safety syringe includes structure which allows the withdrawal of the hypodermic needle into the syringe barrel to minimize the chance of further contact with the sharp needle tip.

One such prior art retractable needle syringe includes a frangible zone which allows the separation of the forward wall of the barrel, which is connected to the hypodermic needle, from the sidewall of the barrel. The syringe also contains structure on the interior of the forward wall and the exterior of the piston for selectively attaching the piston to the forward wall so that the user can forcibly twist the piston to break the frangible structure and draw the forward wall, including the hypodermic needle, into the syringe barrel. This design requires a compromise in the design of the syringe barrel. The barrel must be strong enough to remain intact during normal use yet weak enough to be sheared apart by any user regardless of strength.

The prior art also includes retractable needle syringes. These syringes have structure that engages a needle carrier allowing the needle carrier to be forcibly disengaged from the syringe barrel, by action of the plunger rod, and withdrawn into the syringe barrel. Many prior art retractable needle syringes have deficiencies similar to that described above. In particular, the needle or the needle carrier of the retractable needle syringe must be securely held by the syringe barrel during normal use which often includes substantial hydraulic pressures experienced during injection especially with highly viscous liquids, and forces including piercing rubber stoppers with medication vials. The syringe barrel must hold the needle carrier to a degree that it will not be overcome by the forces of normal use and will still be disengageable through forces applied to a plunger rod which extends from the open proximal end of the syringe barrel. Many prior art retractable needle syringe designs when made with sufficient strength to withstand the forces of normal use have a needle carrier which cannot be easily disengaged. On the other hand, easy disengagement of the needle or the needle carrier can lead to a structure which may not withstand the forces of normal use. This is especially true with needle carriers which are structured to allow a needle assembly to be installed and removed so that the user can select the hypodermic needle size at the time of use. These syringes must also resist the high torque and forces of needle installation and removal. In addition, retractable needle syringes require a two-handed withdrawal procedure which increases the difficulty of use.

The prior art also includes retracting needle syringes which include a spring loaded needle assembly which is held in position during normal use of the syringe assembly and a hollow plunger rod which is sealed during normal use of the syringe assembly so that medication may not enter the plunger rod cavity. These syringes must have structure to allow release of the spring loaded needle and the opening of the plunger rod cavity so that the needle may enter the plunger rod cavity after the syringe is used for its intended purpose. The retracting needle syringes have similar design problems as those recited hereinabove for retractable needle syringes. In particular, the cavity in the plunger rod must be sealed so that medication cannot enter the plunger rod during use. This seal must sometimes withstand high hydraulic pressures when injecting relatively viscous medication through small needles and still be capable of being easily unsealed and to allow access by the needle assembly. Likewise, the needle assembly must be firmly held in place through the forces of injection and still be disengageable so that it may retract into the syringe barrel and into the plunger rod. Some of the prior art retracting needle syringes use plugs to cover the plunger rod cavity leading to an arguably difficult situation since the plug may fail during the injection process. Likewise, some use plugs to hold the needle assembly in place which can arguably become dislodged during use causing fear of the syringe. Further, these designs do not allow for a replaceable needle assembly thus depriving the healthcare worker of the option of choosing the appropriate needle size for the injection or procedure being performed.

Although the prior art teaches many different retractable needle syringes and retracting needle syringes have the capacity to withdraw or allow the needle to enter the syringe barrel or the plunger rod there is still a need for a simple, straight-forward, reliable, easily fabricated retracting needle syringe having a well-sealed plunger rod cavity which can easily be unsealed at the time of needle retracting. There is also a need for a retracting needle syringe having adequate structural integrity to withstand the forces of injection and while the spring can still be easily and intentionally released to allow the needle assembly to enter the plunger rod cavity. There is also a need for a retracting needle syringe having replaceable spring-loaded needle assemblies to allow selecting the proper needle size at the time of use and to facilitate prefilling.

SUMMARY OF THE INVENTION

The present invention relates to an operable retracting needle syringe including a barrel having an inside surface defining a chamber, an open proximal end and an open distal end. A plunger is slidably positioned in fluid-tight engagement with the inside surface of the barrel. The plunger has a distal end, a proximal end, an elongated cavity in the distal end of the plunger and a cover element at the distal end of the plunger sealing the cavity. A needle assembly at the distal end of the barrel includes a needle cannula having a proximal end, a distal end and a lumen therethrough. An inner hub includes an open proximal end and a distal end connected to the proximal end of the needle cannula so that the lumen is in fluid communication with the open proximal end of the hub and the chamber in the barrel. The inner hub includes a flange. An outer hub has a proximal end, a distal end and a passageway therethrough. The flange of the inner hub is connected to the outer hub so that the needle cannula projects distally outwardly from the distal end of the outer hub. A compressed spring is contained between the inner hub and the distal end of the outer hub. A circular release element is movably connected to a proximal end of the flange at a location which separates a dissociable outer portion of the flange from an inner portion of the flange. The release element has a distal end and a sharp proximal end projecting into the chamber of the barrel, wherein distal motion of the plunger with respect to the barrel will cause the sharp proximal end of the release element to contact and cut through the cover element and the distal end of the release element to dissociate the outer portion of the flange from the inner portion of the flange allowing the spring to expand and move the needle cannula far enough into the cavity so that the distal end of the cannula is positioned proximally of the distal end of the outer hub.

Another embodiment of the present invention includes an operable retracting needle assembly for use with a syringe assembly having a barrel with an inside surface defining a chamber, an open proximal end, an open distal end, a circular collar at the distal end having a thread on its surface, a plunger slidably positioned in fluid-tight engagement with the inside surface of the barrel. The plunger has a distal end and a proximal end, an elongated cavity in the distal end of the plunger, and a cover element on the distal end of the plunger sealing the cavity. The needle assembly comprises a needle cannula having a proximal end, a distal end and a lumen therethrough. An inner hub having an open proximal end and a distal end connected to the proximal end of the needle cannula so that the lumen is in fluid communication with the open proximal end of the hub. A flange is positioned on the hub. An outer hub includes a proximal end, a distal end, and a passageway therethrough. The flange is connected to the outer hub so that the needle cannula projects distally outwardly from the distal end of the outer hub. A compressed spring is contained between the inner hub and the outer hub. A discontinuity on the outer hub is shaped to engage the thread on the circular collar so that the needle assembly may be connected and removed from the barrel by rotational movement of the needle assembly with respect to the barrel. A circular release element is movably connected to the proximal end of the flange at a location which separates a dissociable outer portion of the flange from an inner portion of the flange. The release element has a distal end and a sharp proximal end which projects into the chamber of the barrel when the needle assembly is attached to the barrel. An elongated needle shield is removably engaged to the outer hub and covers the needle cannula.

Another embodiment of the present invention includes an operable retracting needle syringe comprising a barrel having an inside surface defining a chamber, an open proximal end, and an open distal end. A plunger is slidably positioned in fluid-tight engagement with the inside surface of the barrel. The plunger has a distal end and a proximal end, an elongated cavity in the distal end of the plunger, and a cover element on the distal end of the plunger sealing the cavity. A needle assembly at the distal end of the barrel includes a needle cannula having a proximal end, a distal end, and a lumen therethrough, an inner hub having an open proximal end and a distal end connected to the proximal end of the needle cannula so that the lumen is in fluid communication with the open proximal end of the hub and the chamber. The inner hub includes a flange. An outer hub connected to the distal end of the barrel has a proximal end, a distal end and a passageway therethrough. The flange is connected to the distal end of the barrel so that the needle cannula projects dismally outwardly from the distal end of the outer hub. A compressed spring is contained between the inner hub and the distal end of the outer hub. A circular release element is movably connected to a proximal end of the flange at a location which separates a dissociable outer portion of the flange from an inner portion of the flange. The release element has a distal end and a sharp proximal end projecting into the chamber, wherein distal motion of the plunger rod with respect to the barrel causes the sharp proximal end of the release element to contact and cut through the cover element and the distal end of the release element to dissociate the outer portion of the flange from the inner portion of the flange allowing the spring to expand and move the needle cannula far enough into the cavity so that the distal end of the needle cannula is positioned proximally of the distal end of the outer hub.

BRIEF DESCRIPTION OF THE DRAWINGS

FIG. 8 is an alternative embodiment of the needle assembly of the present invention.

FIG. 9 is another alternative embodiment of the retracting needle syringe of the present invention.

DETAILED DESCRIPTION

Figure 1:
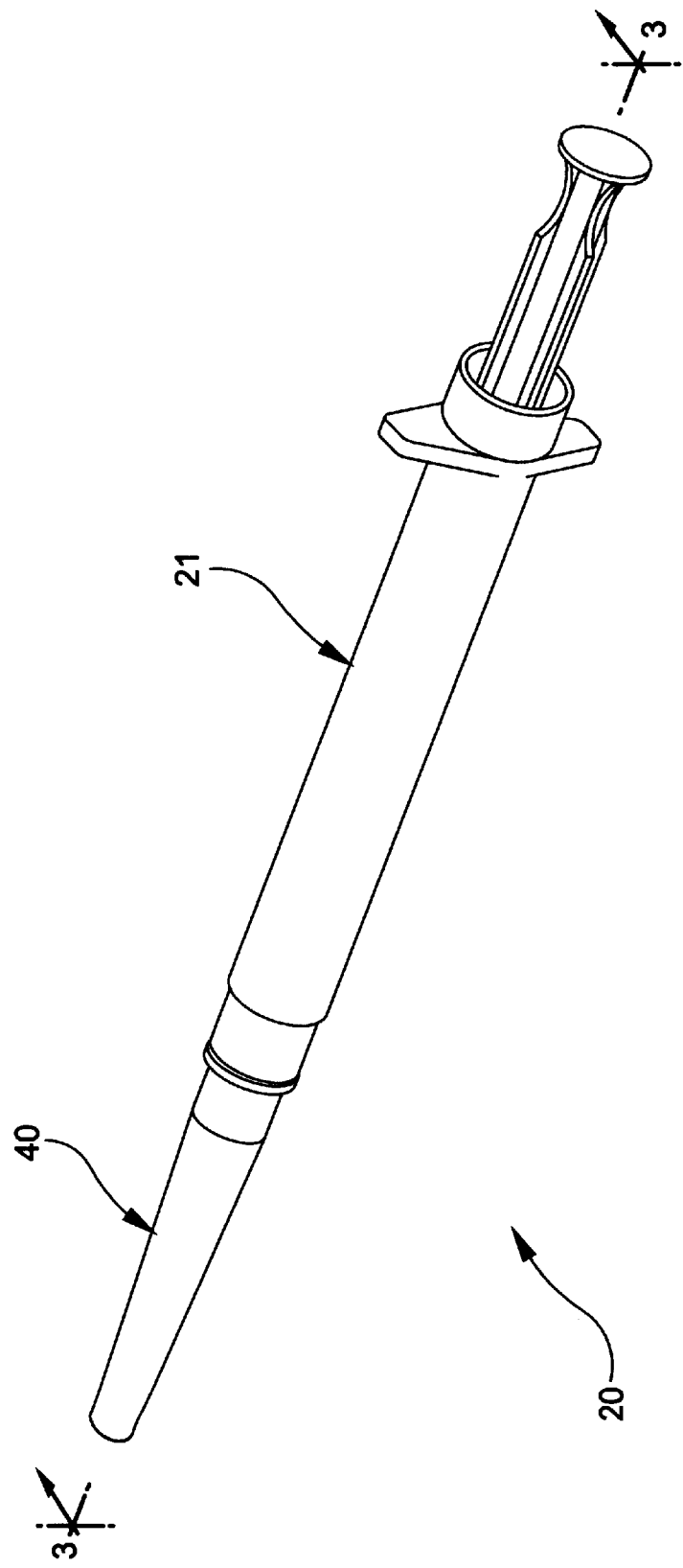
FIG. 1 is a perspective view of the retracting needle syringe of the present invention.
Figure 2:
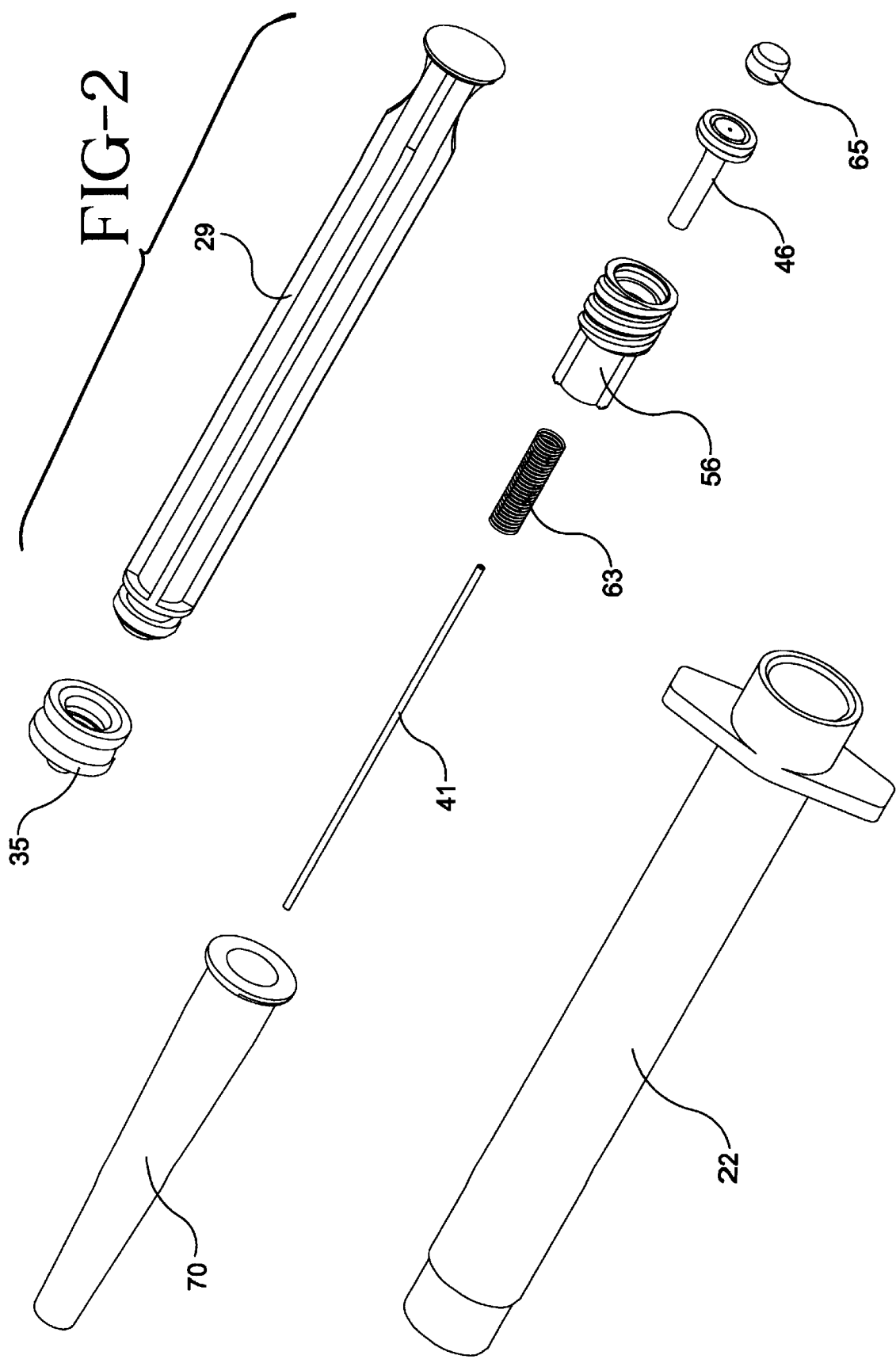
FIG. 2 is an exploded perspective view of the syringe of FIG. 1.
Figure 3:
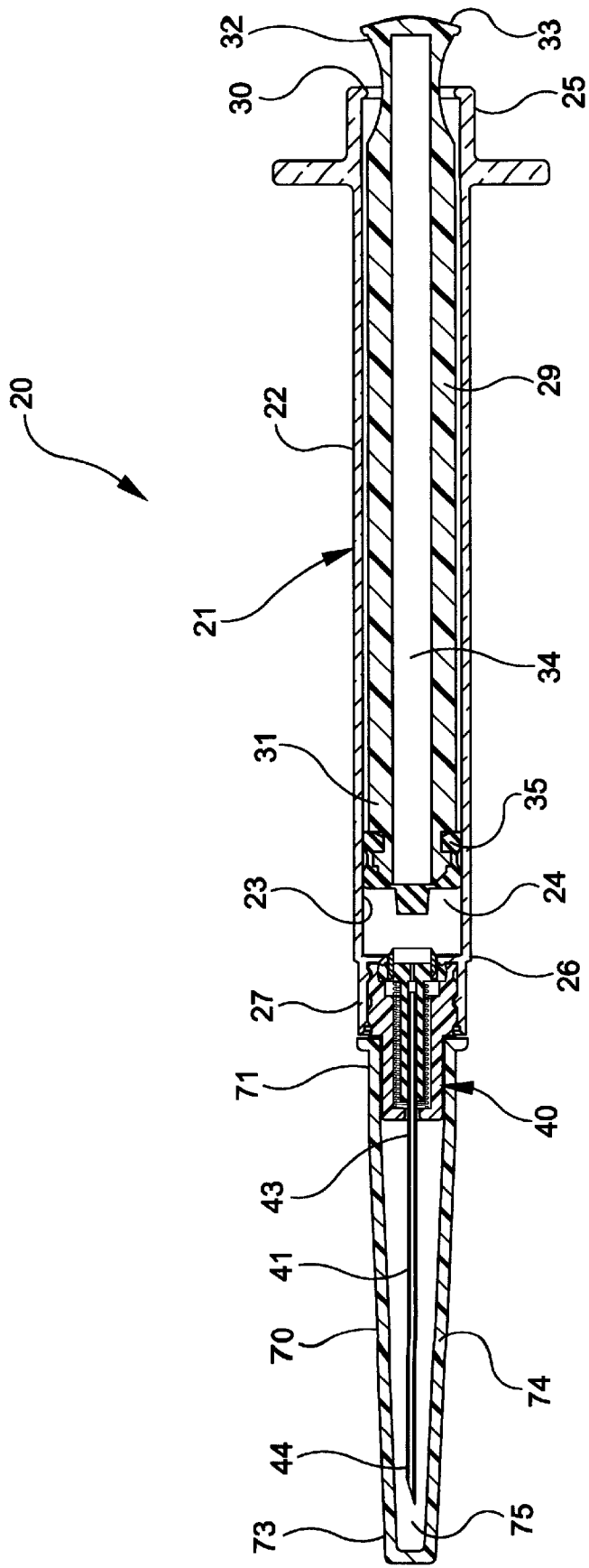
FIG. 3 is a cross-sectional view of the syringe of FIG. 1 taken along line 3—3.
Figure 4:
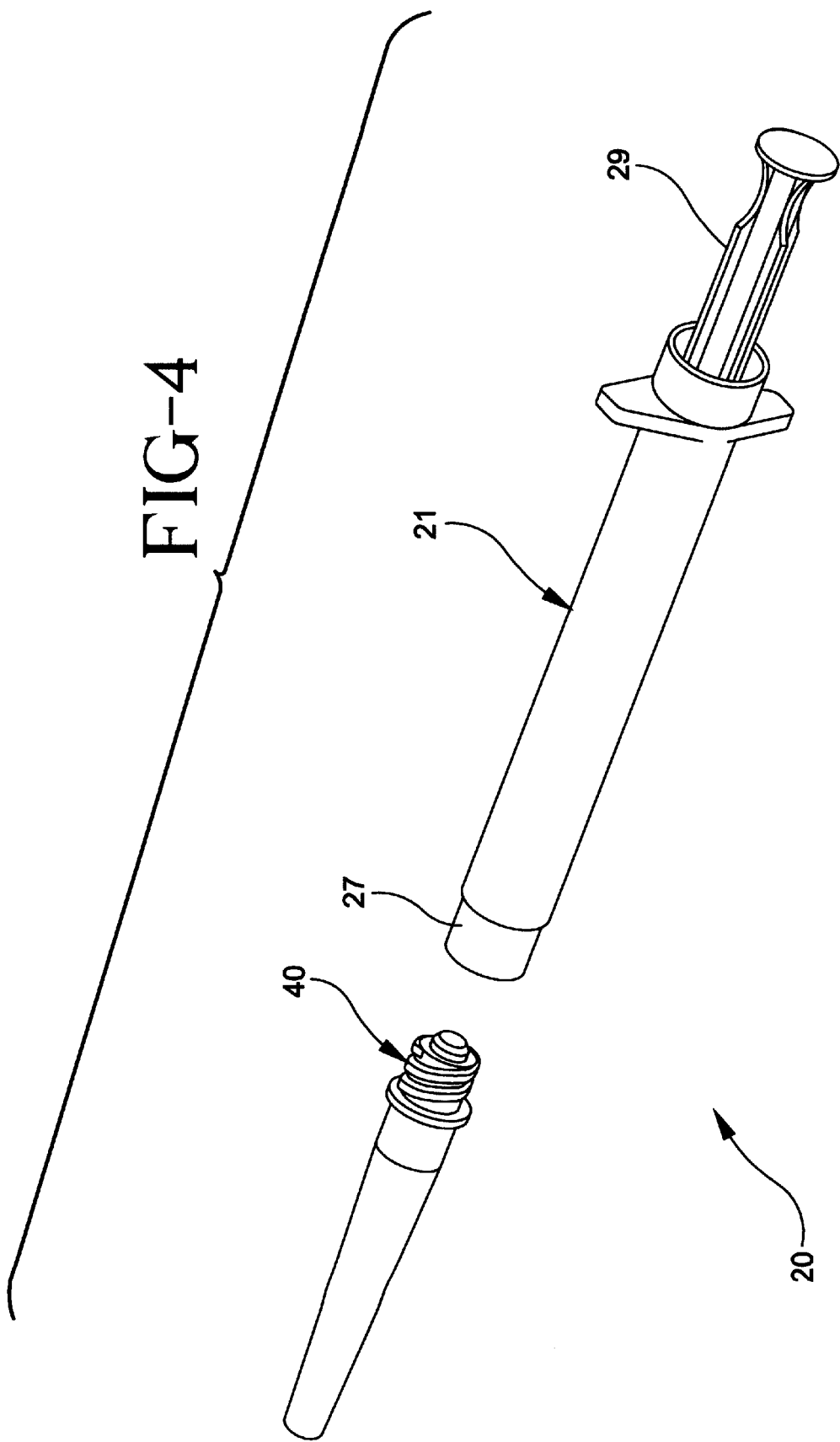
FIG. 4 is the syringe of FIG. 1 illustrating a replaceable needle assembly.

While this invention is satisfied by embodiments in many different forms, there are shown in the drawings and will be herein described in detail, preferred embodiments of the invention with the understanding that the present disclosure is to be considered exemplary of the principles of the invention and not intended to limit the scope of the invention to the embodiments illustrated. The scope of the invention will be measured by the appended claims and their equivalents.

Referring to FIGS. 1–7, an operable retracting needle syringe 20 includes a syringe assembly 21 having a barrel 22 and a plunger 29. The barrel includes inside surface 23 defining a chamber 24, an open proximal end 25 and an open distal end 26. The plunger is slidably positioned in fluid-tight engagement with inside surface 23 of the barrel. The plunger has a distal end 31, a proximal end 32 and an elongated cavity 34 in the distal end of the plunger. In this preferred embodiment, a stopper 35 is positioned on the distal end of the plunger and includes a cover element portion 37 and a sealing portion 38. It is preferred that the cover element 37 further include a projection 39 extending distally outwardly from the cover element. The function of projection 39 will be explained in more detail hereinafter.

Retracting needle syringe 20 also includes a needle assembly 40 at the distal end of the barrel. The needle assembly includes a needle cannula 41 having a proximal end 43, a distal end 44 and a lumen therethrough. An inner hub 46 includes an open proximal end 47 and a distal end 48 which is connected to the proximal end of the needle cannula so that the lumen is in fluid communication with the open proximal end of the hub and chamber 24 of the barrel. Inner hub 46 also includes flange 50.

An outer hub 56 includes a proximal end 57, a distal end 58 and a passageway 59 therethrough. In this preferred embodiment flange 50 is connected directly to outer hub 56 so that needle cannula 41 projects distally outwardly from distal end 58 of the outer hub. In this embodiment, flange 50 is connected to outer hub through a snap-fit arrangement wherein portions of the outside diameter of the hub are larger than the corresponding portions of the inside diameter of the outer hub so that during assembly the inner hub may be pressed to the outer hub and held there securely without additional elements or steps. However, the inner hub flange may be connected to the outer hub in many ways, either directly or indirectly, through the use of adhesives, welding, sheet metal retainers, intermediate elements and the like, and the snap fit arrangement illustrated in the preferred embodiment is merely representative of these many possibilities.

A compressed spring 63 is contained between the inner hub and the distal end of the outer hub. The compressed spring in this embodiment is preferably a coil compression spring. Other types of springs or elastomeric elements may be used to perform the spring function however a coil spring is preferred because of its compact size and the ability to easily design the spring to provide the forces necessary for the proper operation of the present invention.

A circular release element 65 is movably connected to a proximal end 53 of flange 50 at a position which separates a dissociable outer portion 51 of the flange from an inner portion 52 of the flange. The release element includes a distal end 67 and a sharp proximal end 68 projecting into the chamber of the barrel.

Retracting needle syringe 20 preferably, but not necessarily, includes an elongated needle shield having an open proximal end 71, a distal end 73 and a sidewall 74 therebetween defining a recess 75 in the shield. The shield removably engages the syringe and covers the needle cannula. The shield helps protect the needle cannula from contamination before use. In this embodiment, the shield preferably frictionally engages portions of outer hub 56. However, it is within the purview of the present invention to provide a shield which engages portions of the syringe barrel.

In this preferred embodiment, needle assembly 40 is removably attached to barrel 22. To accomplish this result, a circular collar 27 is positioned on the distal end of barrel 22 and includes a thread 28 on its surface which engages a discontinuity 61 on outer hub 56 so that the needle assembly may be removed from the barrel by rotational movement of the needle assembly with respect to the barrel. A wide variety of structures can be provided to allow the removal and attachment of the needle assembly to the barrel. The thread can be placed on the needle assembly and the discontinuity on the collar or both the needle assembly on the collar can have thread-like structures. In addition, the thread or discontinuity on the collar can be on the exterior of the collar and the needle assembly outer hub having an internal structure adapted to engage the external structure on the syringe barrel. A bayonet-type structure can also be provided to connect the needle assembly to the barrel. These structures are all within the purview of the present invention and the structure illustrated is merely representative of these many possibilities.

It is an important feature of this embodiment of the present invention that the needle assembly is removably connected to the barrel. This allows the flexibility to interchange needles and syringes to obtain the appropriately sized needle and syringe combination for the desired drug type and injection site. In addition, the structure of the preferred embodiment allows the installation and removal of the needle assembly from the barrel using the same motions required for the installation and removal of the standard hypodermic needle from a standard hypodermic syringe so that no additional training is required for the healthcare worker.

Figure 5:
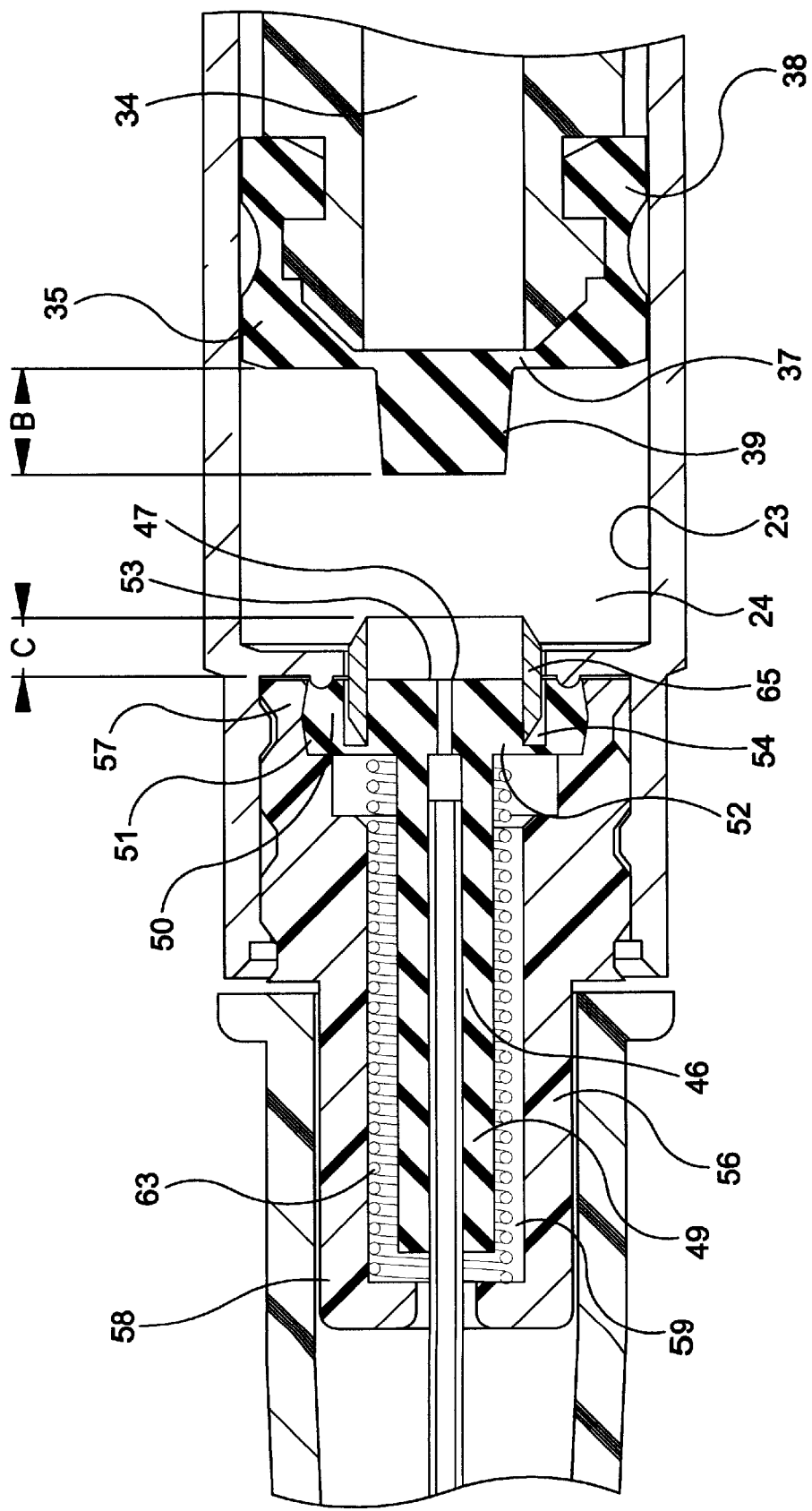
FIG. 5 is an enlarged partial cross-sectional view of the syringe of FIG. 3.
Figure 6:
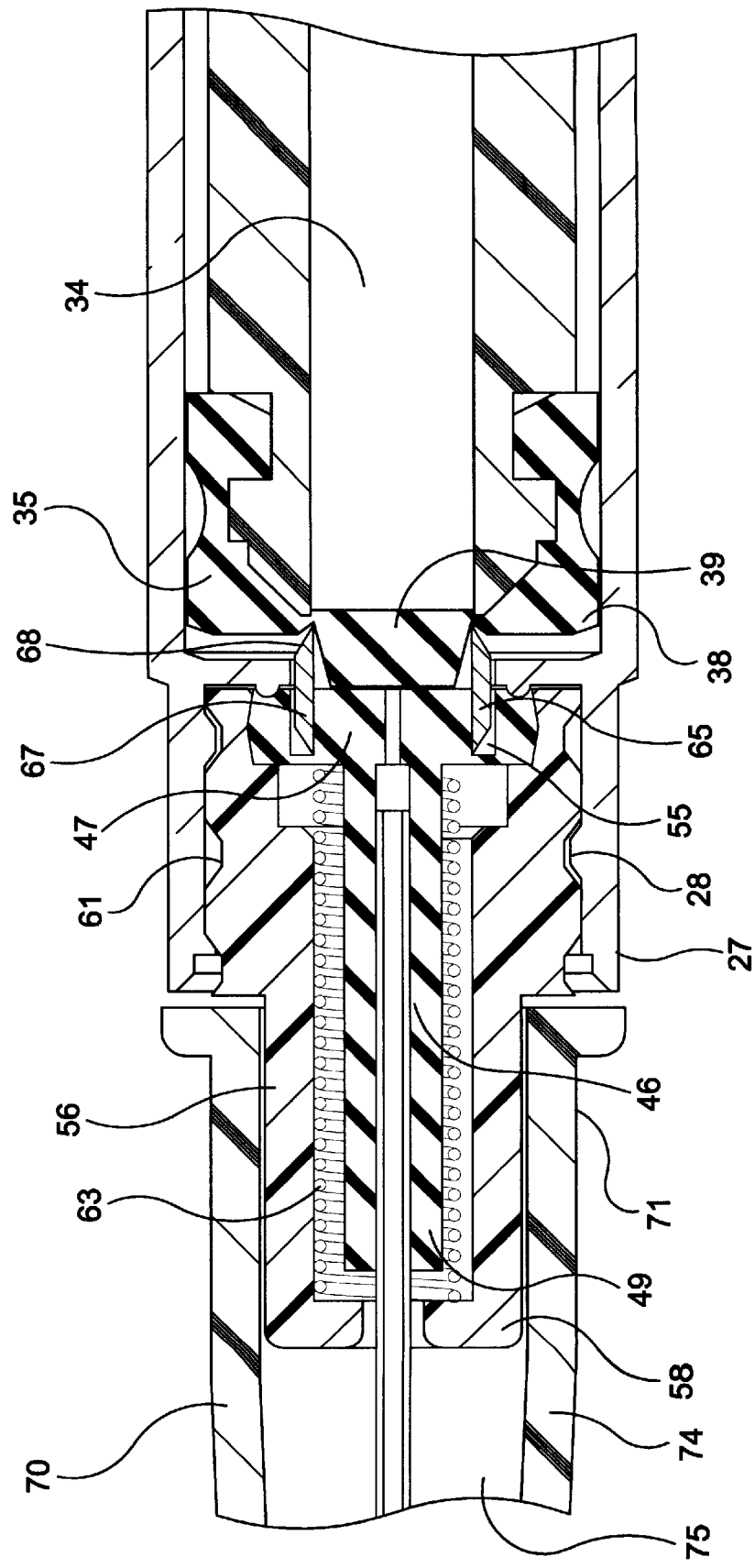
FIG. 6 is an enlarged cross-sectional view of the syringe of FIG. 3 illustrating the cutting of the plunger cover.

In use, the retracting needle syringe of the present invention can be filled using known methods such as withdrawing injectable liquid from a vial having a pierceable stopper. The syringe may then be used to inject liquid into a patient, an I.V. set, a catheter or other suitable delivery device. As best seen in FIGS. 5 and 6 projection 39 is provided on cover element 37 in order to help expel all of the liquid in the chamber. This is another important feature of the present invention since many prior art retractable and retracting needle syringes leave liquid in the barrel at the end of the injection process. Projection 39 is sized and shaped to fit inside release element 65 so that the liquid contained in the volume described by that portion of the release element projecting into the chamber can be expelled through the lumen of the cannula. Many prior art retracting and retractable needle syringes require an additional distal movement of the plunger to allow the withdrawal of the needle cannula into the barrel. The volume of the barrel swept by this additional motion is the volume of wasted medication which can also be expelled into the environment during the needle withdrawal process.

After the liquid in the chamber is injected, the user can apply additional force to the proximal end of the plunger to move the plunger distally with respect to the barrel. This motion will cause the sharp proximal end 68 of release element 65 to contact and cut through cover element portion 37 to open the distal end of elongated cavity 34 so that the needle cannula may enter therein. In this preferred embodiment stopper 35 including cover element portion 37 is made of an elastomeric material selected from the group of thermoplastic elastomers, natural rubbers, synthetic rubber and combinations thereof. Release element 65 is preferably made of a hard material which will hold its sharp edge long enough to cut through the cover element and, as would be explained hereinafter, the flange. A hard plastic may suffice however metal such as stainless steel is preferred.

In the preferred embodiment, as best illustrated in FIG. 5, length B of projection 39 is preferably greater than length C, the distance release element 65 projects into the chamber. Accordingly, when the plunger is moved to its distal position as illustrated in FIG. 6, projection 39 will be compressed and stretched adjacent areas of the cover element making them easier for the release element to cut.

Figure 7:
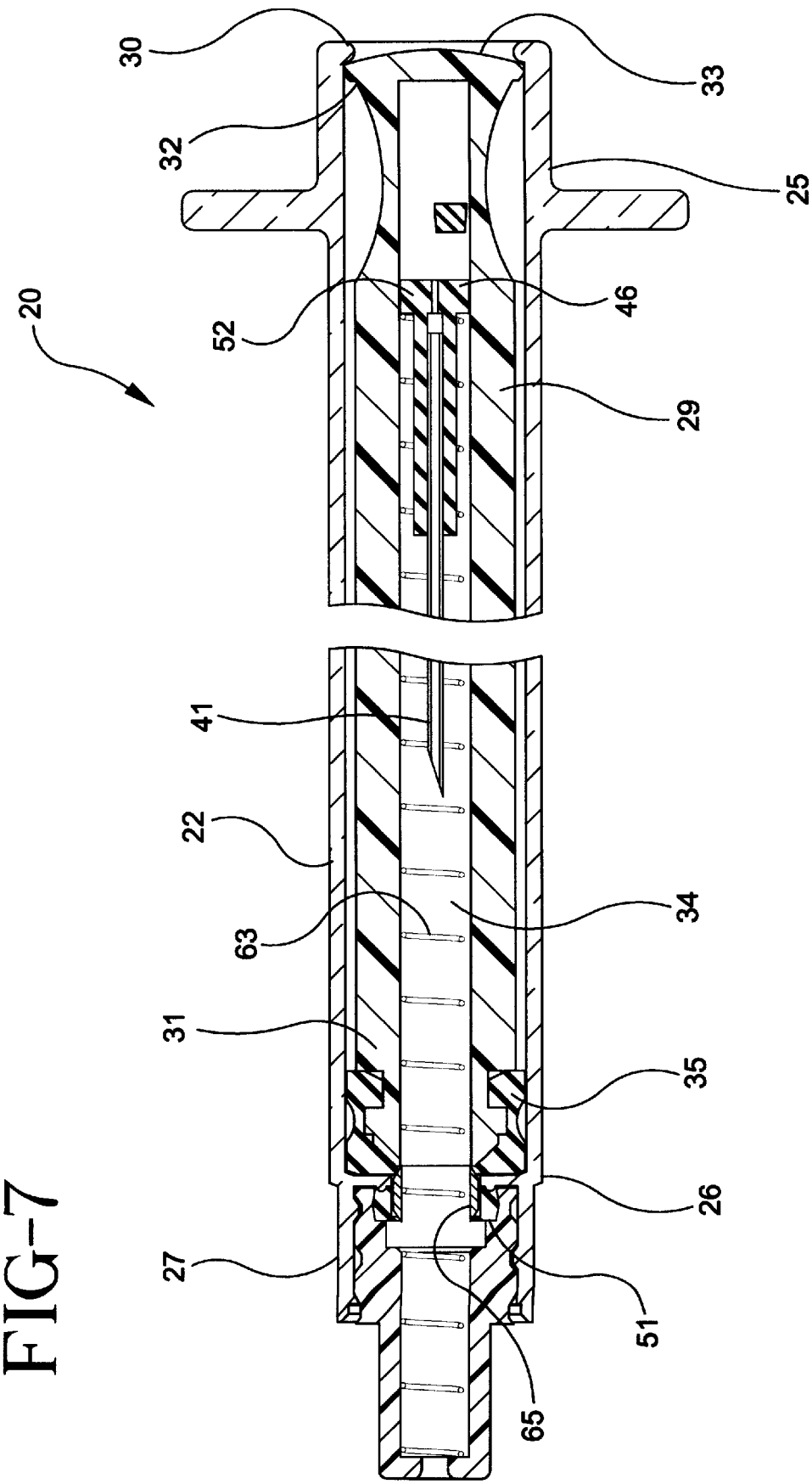
FIG. 7 is an enlarged cross-sectional view illustrating the syringe of FIG. 3 with the needle cannula retracted.

As the plunger is moved distally with respect to the barrel distal end 67 of the release element will dissociate the outer portion 51 of flange 50 from inner portion 52 of the flange allowing the spring to expand and move the needle cannula far enough into the elongated cavity of the plunger, as best illustrated in FIG. 7, so that the distal end of the cannula is positioned proximally of the distal end of the outer hub. In this embodiment, the distal end of the release element includes a sharp distal edge so that the outer portion of the flange is preferably dissociated from the inner portion of the flange by the cutting action of the sharp distal edge of the release element through the thin section 54 of the flange which separates outer portion 51 from inner portion 52. It should be noted that reaction of the contact between the sharp distal edge of the release element and thin section 54 may be cutting, breaking or a combination of both. In this embodiment the release element is partially contained in circular groove 55 of flange 50. The circular groove and the release element are sized and shaped so that the released element is movably connected to the flange through contact of the release element with respect to the circular groove. The circular groove also provides for the thin section 54 which is preferably cut by the release element. Although the release element is shown as a cylindrical metal element with sharp edges on both ends, the release element does not have to be a cylinder but may be a stepped element with the cutting edges having different diameters at each end. This will allow cutting a larger hole in the distal end of the plunger rod and a smaller dimension in the flange so that the flange will more easily fit in the elongated cavity of the plunger.

This structure is one of the important advantages of the present invention over retracting and retractable needle syringes of the prior art. First, in the present invention, as opposed to many retractable needle syringes, the continued motion of the plunger with respect to the barrel is all that is needed to cause the needle assembly or the needle cannula to automatically retract into the syringe barrel. This is a simple one-handed continuation of the injection stroke and it is not a separate process involving rotation of the plunger and pulling the needle back into the barrel. Also, many prior art designs rely on a balance of forces. For example, the distal end of the plunger rod is sealed with a plug which frictionally engages the plunger rod. In this instance, the plug must be secure enough to withstand a sometimes severe hydraulic pressures of injecting viscous medications through small needles and withdrawing the same medication into the syringe. At the same time the plug's connection to the plunger rod must be weak enough so that a person of ordinary strength can cause it to be dislodged at the end of the injection process. This balancing of forces is further complicated by long-term storage wherein the plastic parts will creep and change their size creating the possibility of the distal end of the plunger rod opening before the injection process is complete. This will cause the medication to enter the plunger rod and not the cannula. Likewise, using plugs and other structures to hold the needle in an extended position raises the same issues. In the present invention, distal end of the plunger is securely sealed and the needle cannula is securely positioned in its extended position. At the end of the injection, the additional motion of the plunger rod allows the release element to cut through cover element and the flange. Accordingly, both of these elements can be made much stronger than necessary for sustaining the integrity of the syringe assembly during the injection process and thus insuring against failure due to excessive or unexpected forces. At the end of the process the elements are cut to release them rather than being disengaged. Accordingly, the present design allows for more secure structure for holding the needle cannula in its extended position and for sealing the plunger rod than many prior art structures.

Upon completion of the injection process and the cutting of the cover element and the dissociation of the outer portion of the flange the needle cannula will be propelled into the syringe barrel and plunger so that it no longer protrudes through the distal end of the outer hub. The syringe is now in a condition where it is safe for further handling to deliver to an appropriate disposal device.

Plunger 29 also includes flange 33 at its proximal end. As best illustrated in FIG. 7, the flange is shaped and positioned to be adjacent to the proximal end of the barrel when the plunger is in its distal-most position with respect to the barrel. In this preferred embodiment the flange is preferably flush with or recessed within the proximal end of the barrel so that the user can no longer grab the flange and pull the plunger rod in a proximal direction. This is an important feature of the present invention and helps prevent tampering with the syringe after use and provides a clear indication to the healthcare worker that the syringe is used. The proximal end of the syringe barrel can also contain structure which allows the flange to pass thereby and lock in its distal-most position. In this embodiment, the proximal end of the barrel further includes discontinuities 30. When the plunger is pushed to its distal-most position with respect to the barrel and the needle cannula is released and positioned inside the plunger, flange 33 will be in position to engage discontinuities 30 which will lock the plunger in the barrel and prevent further motion of the plunger with respect to the barrel.

FIG. 8 illustrates an alternative embodiment of the needle assembly of the present invention. Needle assembly 140 includes a needle cannula 141 connected to an inner hub 146 having an open proximal end 147 and a distal end 149 connected to proximal end 143 of the needle cannula so that lumen 145 of the needle cannula is in fluid communication with open proximal end 147. The inner hub also includes flange 150. An outer hub 156 includes a proximal end 157, a distal end 158 and a passageway 159 therethrough. The flange is connected to the proximal end of the outer hub so that the needle cannula projects distally outwardly from the distal end of the outer hub. A spring 163 is contained between the inner hub and the outer hub. A release element 165 is movably connected to the proximal end of flange 150 at a location which separates a dissociable outer portion 151 of the flange from an inner portion 152. The release element includes a sharp proximal end 168 and a distal end 167 which is less sharp than proximal end 168 or blunt. The needle assembly of this embodiment functions similarly to the needle assembly in the embodiment of FIGS. 1–7. When this needle assembly is connected to a syringe which has been used to inject liquid, further distal motion of the plunger with respect to the barrel will cause the sharp proximal end of the release element to contact and cut through the cover element on the plunger. Also, the distal end of the release element will dissociate the outer portion of the flange from the inner portion of the flange for allowing the spring to expand and move the needle cannula into the plunger. In this embodiment, the dissociation of the outer portion of the flange from the inner portion of the flange is caused by breaking thin frangible section 154 which separates the outer and the inner portions of the flange. Accordingly, the flange material should be chosen to be relatively brittle and/or moldable into a thin cross-section which is easily fractured by forces transferred through the release element.

FIG. 9 illustrates another alternative embodiment of the present invention. This embodiment functions similarly to the embodiment of FIGS. 1–7. However, this embodiment is structurally different. In this embodiment, a retracting needle syringe 220 includes a syringe barrel 222 having an inside surface 223 defining a chamber 224. A plunger 229 is positioned in fluid-tight engagement with the inside surface of the barrel. The plunger includes a distal end 231 and an elongated cavity 234 in the distal end. A cover element 237 on the distal end of the plunger seals the cavity. This cover element can be a separate element attached to the distal end of the plunger or it can be integrally molded and formed with the plunger such as through injection molding. A separate element covering the end of the plunger is preferred. Plunger 229 also includes a stopper element in the form of O-ring 230 or other structure which provides for the fluid-tight engagement between the plunger and the inside surface of the barrel. Other structure to provide fluid-tight engagement can include the plunger itself without any intermediate element. A needle assembly 240 at the distal end of the barrel includes a needle cannula 241 having a proximal end 243, a distal end 244 and a lumen therethrough. An inner hub 246 has an open proximal end 247 and a distal end 249 connected to the proximal end of the needle cannula 241 so that the lumen is in fluid communication with the open proximal end of the hub and the chamber. The inner hub also includes a flange 250. An outer hub 256 is connected to distal end 226 of the barrel and includes a proximal end 257, a distal end 258 and a passageway 259 therethrough. Flange 250 is connected to distal end 226 of the barrel so that the needle cannula projects distally outwardly from the distal end of the outer hub. In the embodiment of FIGS. 1–7 the flange on the inner hub is connected directly to the outer hub. In this embodiment, the flange on the inner hub is connected indirectly to the outer hub through the distal end of the syringe barrel. A spring 263 is contained between the inner hub and the distal end of the outer hub. A release element 265 is movably connected to a proximal end of flange 250 at a location which separates a dissociable outer portion 251 of the flange from an inner portion 252. The release element includes a sharp distal end 267 and a sharp proximal end 268. In this embodiment, the outer hub engages the distal end of the barrel through a snap fit arrangement, and the needle assembly is not intended to be removable from the barrel. Also, the inner hub can be integrally formed with the barrel during the time of injection molding of the barrel with the release element being an insert in the molding process. As with the embodiment of FIGS. 1–7 distal motion of the plunger with respect that the barrel will cause the sharp proximal end of the release element to contact and cut through cover element 237 and the distal end of the release element will separate the outer portion and the inner portion allowing the spring to expand and move the needle cannula far enough into the cavity of the plunger so that the distal end of the cannula is positioned proximally of the distal end of the outer hub.

What is claimed is:

1. An operable retracting needle syringe comprising:

a barrel having an inside surface defining a chamber, an open proximal end and an open distal end;

a plunger slidably positioned in fluid-tight engagement with said inside surface of said barrel, said plunger having a distal end and a proximal end, an elongated cavity in said distal end of said plunger, a cover element on said distal end of said plunger sealing said cavity;

a needle assembly at said distal end of said barrel including a needle cannula having a proximal end, a distal end and a lumen therethrough, an inner hub having an open proximal end and a distal end connected to said proximal end of said needle cannula so that said lumen is in fluid communication with said open proximal end of said hub and said chamber, a flange on said hub, an outer hub having a proximal end, a distal end and a passageway therethrough, said flange being connected to said proximal end of said outer hub so that said needle cannula projects distally outwardly from said distal end of said outer hub, a compressed spring contained between said inner hub and said distal end of said outer hub, a release element movably connected to a proximal end of said flange at a location which separates a dissociable outer portion of said flange from an inner portion of said flange, said release element having a distal end and a sharp proximal end projecting into said chamber; and wherein distal motion of said plunger with respect to said barrel will cause said sharp proximal end of said release element to contact and cut through said cover element and said distal end of said release element to dissociate said outer portion of said flange from said inner portion of said flange allowing said spring to expand and move said needle cannula far enough into said cavity so that said distal end of said cannula is positioned proximally of said distal end of said outer hub.

2. The syringe of claim 1 wherein said release element includes a sharp distal edge.

3. The syringe of claim 1 wherein said cover element is a stopper having a side portion which contacts said inside surface of said barrel.

4. The syringe of claim 1 wherein said cover element further includes a projection extending distally outwardly from said cover element, sized and shaped to fit within inside said release element.

5. The syringe of claim 1 wherein said cover element is made of an elastomeric material selected from the group of thermoplastic elastomers, natural rubber, synthetic rubber and combinations thereof.

6. The syringe of claim 1 further including a discontinuity on said outer hub, a circular collar at said distal end of said barrel having a thread which engages said discontinuity on said outer hub so that said needle assembly may be removed from said barrel by rotational movement of said needle assembly with respect to said barrel.

7. The syringe of claim 1 further including a flange on said proximal end of said plunger, said flange being shaped and positioned to be adjacent to said proximal end of said barrel when said plunger is in its distal-most position with respect to said barrel.

8. The syringe of claim 7 further including a discontinuity on said proximal end of said barrel for engaging said flange on said plunger rod when said plunger is in its distal-most position with respect to said barrel to resist proximal motion of said plunger with respect to said barrel.

9. The syringe of claim 1 further including an elongated needle shield removably engaging said syringe and covering said needle cannula.

10. The syringe of claim 1 wherein said spring is a coil spring.

11. The syringe of claim 1 wherein said release element is made of metal.

12. An operable retracting needle syringe comprising:

a barrel having an inside surface defining a chamber, an open proximal end and an open distal end;

a plunger slidably positioned in fluid-tight engagement with said inside surface of said barrel, said plunger having a distal end and a proximal end, an elongated cavity in said distal end of said plunger, a stopper at said distal end of said plunger having a side portion contacting said inside surface and a cover element portion for sealing said cavity;

a needle assembly at said distal end of said barrel including a needle cannula having a proximal end, a distal end and a lumen therethrough, an inner hub having an open proximal end and a distal end connected to said proximal end of said needle cannula so that said lumen is in fluid communication with said open proximal end of said hub and said chamber, a flange on said hub, an outer hub having a proximal end, a distal end and a passageway therethrough, said flange being connected to said proximal end of said outer hub so that said needle cannula projects distally outwardly from said distal end of said outer hub, a compressed spring contained between said inner hub and said distal end of said outer hub, a release element movably connected to a proximal end of said flange at a location which separates a dissociable outer portion of said flange from an inner portion of said flange, said release element having a sharp distal end and a sharp proximal end projecting into said chamber; and wherein distal motion of said plunger with respect to said barrel will cause said sharp proximal end of said release element to contact and cut through said cover element and said sharp distal end of said release element to cut through said flange to said outer portion of said flange from said inner portion of said flange allowing said spring to expand and move said needle cannula far enough into said cavity so that said distal end of said cannula is positioned proximally of said distal end of said outer hub.

13. The syringe of claim 12 further including a discontinuity on said outer hub, a circular collar at said distal end of said barrel having a thread which engages said discontinuity on said outer hub so that the needle assembly may be removed from said barrel by rotational movement of the needle assembly with respect to said barrel.

14. The syringe of claim 12 further including a flange on said proximal end of said plunger, said flange being shaped and positioned to be adjacent to said proximal end of said barrel when said plunger is in its distal-most position with respect to said barrel.

15. The syringe of claim 12 wherein said cover element further includes a projection extending distally outwardly from said cover element, sized and shaped to fit within inside said release element.

16. The syringe of claim 12 wherein said spring is a coil spring.

17. An operable retracting needle assembly for use with a syringe assembly including a barrel having an inside surface defining a chamber, an open proximal end, an open distal end, a circular collar at said distal end having a thread on its surface, a plunger slidably positioned in fluid-tight engagement with said inside surface of said barrel, said plunger having a distal end and a proximal end, an elongated cavity in said distal end of said plunger, and a cover element on said distal end of said plunger sealing said cavity, comprising:

a needle cannula having a proximal end, a distal end and a lumen therethrough, an inner hub having an open proximal end and a distal end connected to said proximal end of said needle cannula so that said lumen is in fluid communication with said open proximal end of said hub, a flange on said hub, an outer hub having a proximal end, a distal end and a passageway therethrough, said flange being connected to said proximal end of said outer hub so that said needle cannula projects distally outwardly from said distal end of said outer hub, a compressed spring contained between said inner hub and said distal end of said outer hub, a discontinuity on said outer hub positioned and shaped to engage said thread on said barrel so that said needle assembly may be connected and removed from said barrel by rotational movement of said needle assembly with respect to said barrel, and a circular release element movably connected to a proximal end of said flange at a location which separates a dissociable outer portion of said flange from an inner portion of said flange, said release element having a distal end and a sharp proximal end for projecting into said chamber.

18. The needle assembly of claim 17 wherein said release element includes a sharp distal edge (for dissociation of said outer flange from said inner flange by cutting action of said sharpened distal end).

19. The needle assembly of claim 17 further including an elongated needle shield removably engaging said outer hub and covering said needle cannula.

20. An operable retracting needle assembly for use with a syringe assembly including a barrel having an inside surface defining a chamber, an open proximal end, an open distal end, a circular collar at said distal end having a thread on its surface, a plunger slidably positioned in fluid-tight engagement with said inside surface of said barrel, said plunger having a distal end and a proximal end, an elongated cavity in said distal end of said plunger, and a cover element on said distal end of said plunger sealing said cavity, comprising:

a needle cannula having a proximal end, a distal end and a lumen therethrough, an inner hub having an open proximal end and a distal end connected to said proximal end of said needle cannula so that said lumen is in fluid communication with said open proximal end of said hub, a flange on said hub, an outer hub having a proximal end, a distal end and a passageway therethrough, said flange being connected to said proximal end of said outer hub so that said needle cannula projects distally outwardly from said distal end of said outer hub, a compressed spring contained between said inner hub and said distal end of said outer hub, a discontinuity on said outer hub positioned and shaped to engage said thread on said collar so that said needle assembly may be connected and removed from said barrel by rotational movement of said needle assembly with respect to said barrel, and a circular release element movably connected to a proximal end of said flange at a location which separates a dissociable outer portion of said flange from an inner portion of said flange, said release element having a distal end and a sharp proximal end for projecting into said chamber and an elongated needle shield removably engaging said outer hub and covering sad needle cannula.

21. The needle assembly of claim 20 wherein said release element includes a sharp distal edge.

22. An operable retracting needle syringe comprising:

a barrel having an inside surface defining a chamber, an open proximal end and an open distal end;

a plunger slidably positioned in fluid-tight engagement with said inside surface of said barrel, said plunger having a distal end and a proximal end, an elongated cavity in said distal end of said plunger, a cover element on said distal end of said plunger sealing said cavity;

a needle assembly at said distal end of said barrel including a needle cannula having a proximal end, a distal end and a lumen therethrough, an inner hub having an open proximal end and a distal end connected to said proximal end of said needle cannula so that said lumen is in fluid communication with said open proximal end of said hub and said chamber, a flange on said hub, an outer hub connected to said distal end of said barrel having a proximal end, a distal end and a passageway therethrough, said flange being connected to said distal end of said barrel so that said needle cannula projects distally outwardly from said distal end of said outer hub, a compressed spring contained between said inner hub and said distal end of said outer hub, a release element movably connected to a proximal end of said flange at a location which separates a dissociable outer portion of said flange from an inner portion of said flange, said release element having a distal end and a sharp proximal end projecting into said chamber; and wherein distal motion of said plunger with respect to said barrel will cause said sharp proximal end of said release element to contact and cut through said cover element and said distal end of said release element to dissociate said outer portion of said flange from said inner portion of said flange allowing said spring to expand and move said needle cannula far enough into said cavity so that said distal end of said cannula is positioned proximally of said distal end of said outer hub.

23. The syringe of claim 22 wherein said release element includes a sharp distal edge (for dissociation of said outer flange from said inner flange by cutting action of said sharpened distal end).

24. The syringe of claim 22 wherein said cover element is a stopper having a side portion which contacts said inside surface of said barrel.

25. The syringe of claim 22 wherein said cover element further includes a projection extending distally outwardly from said cover element, sized and shaped to fit within inside said release element.

26. The syringe of claim 22 wherein said cover element is made of an elastomeric material selected from the group of thermoplastic elastomers, natural rubber, synthetic rubber and combinations thereof.

27. The syringe of claim 22 further including a flange on said proximal end of said plunger, said flange being shaped and positioned to be adjacent to said proximal end of said barrel when said plunger is in its distal-most position with respect to said barrel.

28. The syringe of claim 22 further including an elongated needle shield removably engaging said syringe and covering said needle cannula.

29. The syringe of claim 22 wherein said spring is a coil spring.

30. The syringe of claim 22 wherein said release element is made of metal.

31. An operable retracting needle syringe comprising:

a barrel having an inside surface defining a chamber, an open proximal end and an open distal end;

a plunger slidably positioned in fluid-tight engagement with said inside surface of said barrel, said plunger having a distal end and a proximal end, an elongated cavity in said distal end of said plunger, a cover element on said distal end of said plunger sealing said cavity;

a needle assembly at said distal end of said barrel including a needle cannula having a lumen therethrough, an inner hub having an open proximal end and a distal end connected to said needle cannula so that said lumen is in fluid communication with said open proximal end of said hub and said chamber, a flange on said hub having a dissociable outer portion and an inner portion, an outer hub having a proximal end, a distal end and a passageway therethrough, said flange being connected to said proximal end of said outer hub so that said needle cannula projects distally outwardly from said distal end of said outer hub, a compressed spring contained between said inner hub and said said outer hub, means in said distal end of said barrel for cutting through said cover element and dissociating said outer portion of said flange from said inner portion of said flange for allowing said spring to expand and move said needle cannula far enough into said cavity so that said cannula is positioned proximally of said distal end of said outer hub.

32. The syringe of claim 31 wherein said cover element is a stopper having a side portion which contacts said inside surface of said barrel.

33. The syringe of claim 31 further including means for allowing the removal of said needle assembly from said barrel by rotational movement of said needle assembly with respect to said barrel.

34. The syringe of claim 31 further including a flange on said proximal end of said plunger, said flange being shaped and positioned to be adjacent to said proximal end of said barrel when said plunger is in its distal-most position with respect to said barrel.

* * * * *